(12) United States Patent
Zhang et al.

(10) Patent No.: US 9,429,542 B2
(45) Date of Patent: Aug. 30, 2016

(54) SIGNAL EXTRACTION CIRCUITS AND METHODS FOR ION MOBILITY TUBE, AND ION MOBILITY DETECTORS

(71) Applicants: Nutech Company Limited, Beijing (CN); Tsinghua University, Beijing (CN)

(72) Inventors: Qingjun Zhang, Beijing (CN); Zhiqiang Chen, Beijing (CN); Yuanjing Li, Beijing (CN); Ziran Zhao, Beijing (CN); Yinong Liu, Beijing (CN); Shiping Cao, Beijing (CN); Xiang Zou, Beijing (CN); Xianghua Li, Beijing (CN); Jianping Chang, Beijing (CN); Shuqiang Dong, Beijing (CN); Yan Zheng, Beijing (CN)

(73) Assignees: Nuctech Company Limited, Beijing (CN); Tsinghua University, Beijing (CN)

(*) Notice: Subject to any disclaimer, the term of this patent is extended or adjusted under 35 U.S.C. 154(b) by 103 days.

(21) Appl. No.: 13/983,334

(22) PCT Filed: Dec. 28, 2012

(86) PCT No.: PCT/CN2012/087863
§ 371 (c)(1),
(2) Date: Aug. 2, 2013

(87) PCT Pub. No.: WO2013/102420
PCT Pub. Date: Jul. 11, 2013

(65) Prior Publication Data
US 2013/0313426 A1  Nov. 28, 2013

(30) Foreign Application Priority Data
Jan. 6, 2012  (CN) .......................... 2012 1 0003936

(51) Int. Cl.
*G01N 27/62* (2006.01)

(52) U.S. Cl.
CPC ................... *G01N 27/622* (2013.01)

(58) Field of Classification Search
CPC ...................................................... G01N 27/622
USPC ................................................. 250/281–300
See application file for complete search history.

(56) References Cited

U.S. PATENT DOCUMENTS 5,180,984 A * 1/1993 Murata et al. ................. 324/399
7,838,823 B1  11/2010 Pfeifer et al.
(Continued)

FOREIGN PATENT DOCUMENTS

| CN | 101937823 | 1/2011 |
| CN | 102592938 | 7/2012 |
| CN | 202487527 | 10/2012 |

OTHER PUBLICATIONS

International Search Report for PCT Application No. PCT/CN2012/087863, dated Apr. 4, 2013, 5 pages.
(Continued)

*Primary Examiner* — Robert Kim
*Assistant Examiner* — Eliza Osenbaugh-Stewar
(74) *Attorney, Agent, or Firm* — Westman, Champlin & Koehler, P.A.

(57) ABSTRACT

Embodiments of the present disclosure relate to substance detection technology, and to signal extraction circuits and methods for ion mobility tubes, and ion mobility detectors, which can solve the problem with the conventional technologies that it is difficult to design and manufacture the leadout circuit for the pulsed voltage on the Faraday plates. A signal extraction circuit for an ion mobility tube includes an DC-blocking module configured to remove a DC voltage contained in a voltage extracted, by a signal leadin terminal, from the Faraday plate, and to output, by a signal leadout terminal, a pulsed voltage contained in the voltage extracted from the Faraday plate. An ion mobility detector includes the signal extraction circuit for an ion mobility tube according to the present invention. A signal extraction method for an ion mobility tube includes extracting a voltage on a Faraday plate in the ion mobility tube, removing a DC voltage contained in the voltage extracted from the Faraday plate, and outputting a pulsed voltage contained in the voltage extracted from the Faraday plate. The present invention is used to extract a pulsed voltage from the Faraday plate.

7 Claims, 2 Drawing Sheets

(56) References Cited

U.S. PATENT DOCUMENTS

| | | |
|---|---|---|
| 2005/0087699 A1* | 4/2005 | Miyake ................... 250/492.1 |
| 2005/0109930 A1 | 5/2005 | Hill, Jr. et al. |
| 2010/0252729 A1* | 10/2010 | Jolliffe et al. ............. 250/282 |
| 2011/0168884 A1* | 7/2011 | Li et al. ................... 250/288 |
| 2011/0297837 A1* | 12/2011 | Ishitsu et al. .......... 250/370.08 |
| 2012/0228490 A1* | 9/2012 | Wu et al. ................. 250/282 |

OTHER PUBLICATIONS

Written Opinion for International Search Report for PCT Application No. PCT/CN2012/087863, dated Apr. 4, 2013, 5 pages.

* cited by examiner

SIGNAL EXTRACTION CIRCUITS AND METHODS FOR ION MOBILITY TUBE, AND ION MOBILITY DETECTORS

CROSS-REFERENCE TO RELATED APPLICATION

This Application is a Section 371 National Stage Application of International Application No. PCT/CN2012/087863, filed 28 Dec. 2012, which claims priority to Chinese Application No. 201210003936.0, filed Jan. 6, 2012, the contents of which are hereby incorporated by reference in their entirety.

TECHNICAL FIELD

The present application relates to substance inspection technology, and more particularly to signal extraction circuits and methods for ion mobility tubes, and ion mobility detectors that configure and uses the signal extraction circuits and methods.

BACKGROUND

It will be very useful to detect types and categories of unknown substances with various new technologies. An example is recently using ion mobility technology to detect dangerous articles, such as explosives, or drugs, in the market of safety inspection, to prevent such dangerous articles from entering public places.

Currently, ion mobility detectors (or ion mobility spectrometer) that use ion mobility technology to detect dangerous articles are classified, based on different ion polarities to be detected, into positive-mode ion mobility detectors for detecting positive ions and negative-mode ion mobility detectors for detecting negative ions. The detection coverage (application) of such ion mobility detectors is limited due to positive and negative modes of ions. While most molecules have specific electroaffinity, a few of molecules can produce both positive and negative ions at the same time. Dual-mode ion mobility detectors (or dual-polarity IMS) equipped with respective positive and negative mobility zones have been developed in order to expand the coverage of detection with ion mobility technology. Such ion mobility detectors are large-sized, and have larger detection coverage and higher resolution. The ion mobility detectors in market generally appear as a set of machine, and cost more than single-mode ion mobility detectors.

The conventional dual-mode ion mobility detector primarily consists of an ion source, a positive ion gate, a negative ion gate, two drift tubes (TOF), and two Faraday plates. The simplest configuration is locating the two drift tubes on the respective sides of the ion source. The potential of the ion source is generally ground potential (i.e., potential of zero) since the electric fields of the positive and negative mobility zones have the same direction. The amplitude of a pulsed voltage is decided by quantity of electric charges carried by an ion cluster arriving at the Faraday plates, and usually reflects the number of collected ions. Accordingly, it is possible to determine the particular type of some substance by analyzing variations of the pulsed voltage. To ensure sufficient electric field strength between the Faraday plates and the ion source, the Faraday plates are placed at a high potential of several thousand volts (often around 3,000V), and circuits connected behind the Faraday plates, such as a leadout circuit for the pulsed voltage (often about several millivolts), an amplification circuit and an analog-to-digital conversion circuit for the pulsed voltage, are floating at a high potential of several thousand volts.

Conventionally, transforms are used to transform a high voltage of several thousand volts to the zero potential, that is, setting amplification and shaping circuits at backend as floating at a high voltage of several thousand volts, and then extracting an amplified pulsed electric signal through an isolation device. Since such high voltage up to several thousand volts has a strict requirement on resistance against high voltage, there are only a narrow range of electronic devices that can be selected for the transformer. Moreover, circuits within the transformer and peripheral leadout circuits electrically connected to the transformer are complex. As a result, it is difficult to design and manufacture the leadout circuit for the pulsed voltage on the Faraday plates, leading to difficulties in digitalization and subsequent processing of the pulsed voltage signal.

SUMMARY

Objects of the present application are to provide signal extraction circuits for ion mobility tubes, ion mobility detectors that configure the signal extraction circuits, and signal extraction methods for ion mobility tubes, to solve the problem with the conventional technologies that it is difficult to design and manufacture the leadout circuit for the pulsed voltage on the Faraday plates.

To achieve the above objects, a signal extraction circuit for an ion mobility tube according to the present disclosure comprises an DC-blocking module provided with a signal leadin terminal and a signal leadout terminal, wherein the signal leadin terminal is electrically connected to a Faraday plate within the ion mobility tube; the DC-blocking module is configured to remove a DC voltage contained in a voltage extracted, by the signal leadin terminal, from the Faraday plate, and to output, by the signal leadout terminal, a pulsed voltage contained in the voltage extracted from the Faraday plate.

Preferably, the DC-blocking module comprises at least two capacitors connected in series or in parallel with each other. The signal leadin terminal is connected to one of a positive polarity or a negative polarity of the capacitors, and the signal leadout terminal is connected to the other of the positive or negative polarity of the capacitors.

Preferably, the at least capacitors are connected in series, and each of the capacitors has a capacitance of 5 nf to 20 nf.

An ion mobility detector according to embodiments of the present disclosure comprises an ion mobility tube;
 the signal extraction circuit for an ion mobility tube as described in the above embodiments, wherein the signal leadin terminal is electrically connected to the Faraday plate within the ion mobility tube;
 a pulsed voltage processing circuit electrically connected to the signal leadout terminal and configured to perform amplification and shaping and/or analog-to-digital conversion on the pulsed voltage output from the signal leadout terminal.

Preferably, an outer shield hood and an inner shield hood are further provided within the ion mobility tube.

The Faraday plate comprises first and second sides located opposite to each other, and the first side is configured to receive ions.

The outer shield hood is disposed covering the Faraday plate, and a convex part of the outer shield hood is located opposite to the second side of the Faraday plate.

The Faraday plate is electrically connected to an inner core of a first coaxial cable via a connection core wire.

The inner shield hood is located inside the outer shield hood, and a convex part of the inner shield hood is located opposite to the second side of the Faraday plate and disposed covering the connection core wire.

The inner core of the first coaxial cable is electrically connected in parallel to each of the signal leadin terminal and a first power supply terminal of the ion mobility tube.

Both ends of a first outer conductor of the first coaxial cable are electrically connected to each of the outer shield hood and a second power supply terminal of the ion mobility tube.

Both ends of a second outer conductor of the first coaxial cable are electrically connected to each of the inner shield hood and the first power supply terminal.

Preferably, at least one resistor is connected in series between the first power supply terminal of the ion mobility tube and the first coaxial cable.

Preferably, one of the polarities of at least one filter capacitor is further electrically connected between the first power supply terminal of the ion mobility tube and the inner core and the second outer conductor of the first coaxial cable, and the other polarity of the filter capacitor is grounded.

Preferably, the first and second power supply terminals of the ion mobility tube are electrically connected to different high-voltage power supplies via two core wires of a two-core cable, respectively. An outer shield layer of the two-core cable is grounded.

Preferably, the resistor has a resistance of 400 to 600 MΩ.

Preferably, the signal leadout terminal is electrically connected to a second coaxial cable, and the pulsed voltage output from the signal leadout terminal is output from an inner core of the second coaxial cable. An outer conductor of the second coaxial cable is grounded.

Preferably, the first and second coaxial cables are each a tri-coaxial cable. The first outer conductor is an outer shield layer of the tri-coaxial cable, and the second outer conductor is an inner signal layer of the tri-coaxial cable.

Preferably, the signal extraction circuit for the ion mobility tube is provided on a circuit board, and packaged together with the circuit board in a potting glue. The potting glue is further covered with a grounded metal shield hood.

Preferably, the ion mobility detector is a dual-mode ion mobility detector having positive and negative ion mobility zones.

A signal extraction method for an ion mobility tube according to embodiments of the present disclosure comprises the following steps:

extracting a voltage on a Faraday plate in the ion mobility tube;

removing a DC voltage contained in the voltage extracted from the Faraday plate, and outputting a pulsed voltage contained in the voltage extracted from the Faraday plate.

Any of the above solutions according to embodiments of the present disclosure can provide at least the following effects.

In the embodiments of the present disclosure, after extracting from the Faraday plate a voltage on the Faraday plate within the ion mobility tube, the pulsed voltage in the output voltage is eventually obtained by removing the DC voltage from the voltage output from the Faraday plate, and outputting the pulsed voltage in the voltage output from the Faraday plate. In this way, there is no need for transformation of the voltage of several thousand volts on the Faraday plate during the leadout of the pulsed voltage, and thus no need for using any transformer having complex internal and peripheral circuits. Meanwhile, Removing the DC voltage and extracting the pulsed voltage can be achieved by using the DC-blocking (or DC-blocking and AC-passing or AC-passing and DC-blocking) module or any other circuit having such DC-blocking and AC-passing function. Compared with withstanding and transforming the voltage of several thousand volts on the Faraday plate, it is much easier to removing the DC voltage, and thus the internal circuit structure of the DC-blocking module or any other circuit having such DC-blocking and AC-passing function will be much simpler. This reduces difficulties in design and manufacture processes, and makes the digitalization and subsequent processing of the pulsed voltage signal much easier. In this way, the above solutions solve the problem with the conventional technologies that it is difficult to design and manufacture the leadout circuit for the pulsed voltage on the Faraday plates.

BRIEF DESCRIPTION OF THE DRAWINGS

Figures illustrated herein are intended for further understanding of the present invention, and constitute part of the present application. Illustrative embodiments of the present disclosure and description thereof are intended for explaining, other than inappropriately limiting, the present invention. In the figures.

DETAILED DESCRIPTION OF THE EMBODIMENTS

In the following, solutions of the present disclosure will be further explained with reference to the figures and embodiments.

Embodiments of the present disclosure provide a simple-structure and low-cost signal extraction circuit for an ion mobility tube, an ion mobility detector having the signal extraction circuit disposed therein, and a signal extraction method used in the signal extraction circuit.

Figure 1:
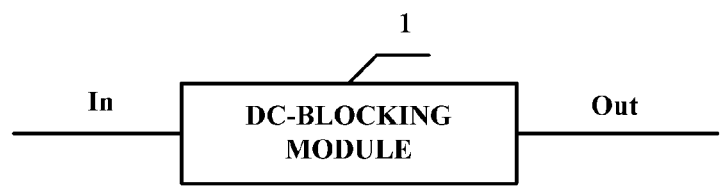
FIG. 1 is a schematic diagram showing connections between internal components of a signal extraction circuit for an ion mobility tube according to embodiments of the present disclosure.

As shown in FIG. 1, a signal extraction circuit for an ion mobility tube according to an embodiment of the present disclosure includes a DC-blocking module 1 provided with a signal leadin terminal In and a signal leadout terminal Out.

Figure 2:
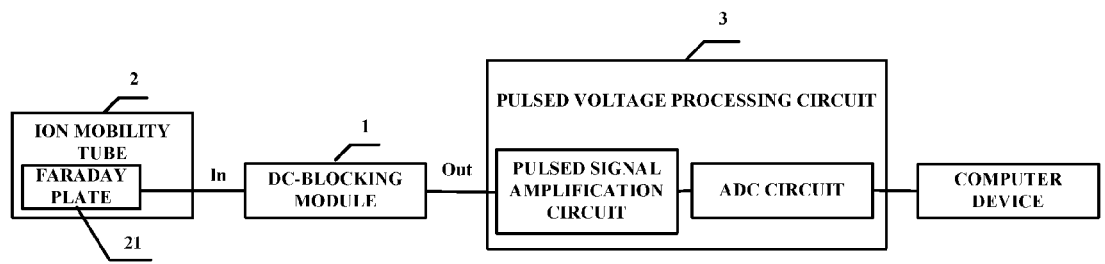
FIG. 2 is a schematic diagram showing connects between an ion mobility tube and a signal extraction circuit for the ion mobility tube and other peripheral circuits in an ion mobility detector according to embodiments of the present disclosure.
Figure 3:
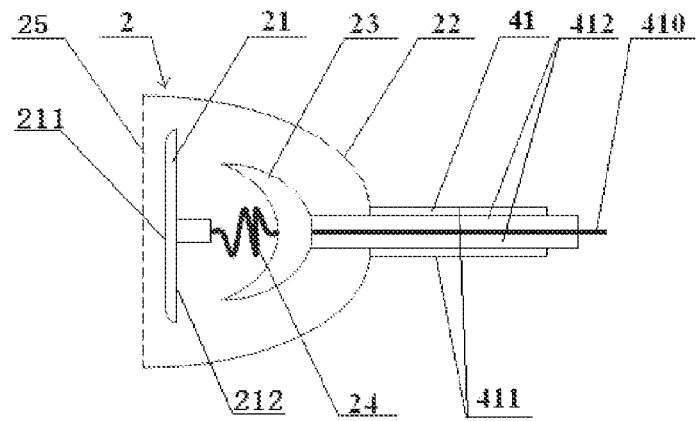
FIG. 3 is a schematic diagram showing connects between an ion mobility tube and a first coaxial cable in an ion mobility detector according to embodiments of the present disclosure.

The signal leadin terminal In is electrically connected to a Faraday plate 21 within an ion mobility tube 2 shown in FIG. 2 or 3.

The DC-blocking module 1 is configured to remove a DC voltage contained in a voltage extracted from the Faraday plate 21 by the signal leadin terminal In, and output from the signal leadout terminal Out a pulsed voltage in the voltage extracted from the Faraday plate 21 by the signal leadin terminal In.

In the embodiment of the present disclosure, after extracting from the Faraday plate 21 a voltage on the Faraday plate 21 within the ion mobility tube 2 shown in FIG. 2 or 3, the pulsed voltage in the output voltage is eventually obtained by removing the DC voltage from the voltage output from the Faraday plate 21, and outputting the pulsed voltage in the voltage output from the Faraday plate 21. In this way, there is no need for transformation of the voltage of several thousand volts on the Faraday plate 21 during the leadout of the pulsed voltage, and thus no need for using any transformer having complex internal and peripheral circuits. Meanwhile, Removing the DC voltage and extracting the pulsed voltage can be achieved by using the DC-blocking (or DC-blocking and AC-passing or AC-passing and DC-blocking) module or any other circuit having such DC-blocking and AC-passing function. Compared with withstanding and transforming the voltage of several thousand volts on the Faraday plate 21, it is much easier to removing the DC voltage, and thus the internal circuit structure of the DC-blocking module 1 or any other circuit having such DC-blocking and AC-passing function will be much simpler. This reduces difficulties in design and manufacture processes, and makes the digitalization and subsequent processing of the pulsed voltage signal much easier. In this way, the above solutions solve the problem with the conventional technologies that it is difficult to design and manufacture the leadout circuit for the pulsed voltage on the Faraday plates.

Figure 4:
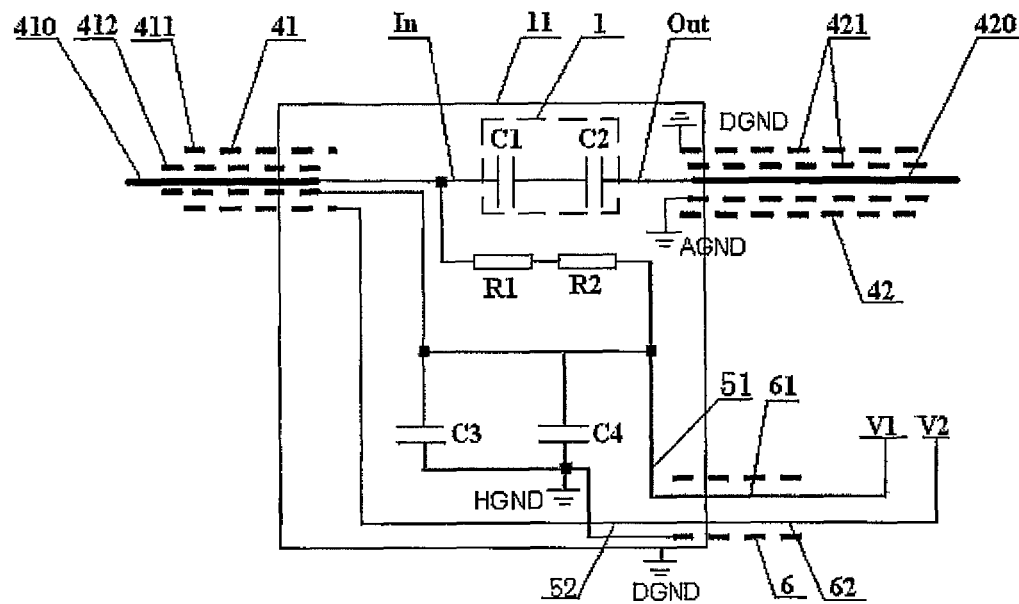
FIG. 4 is a schematic diagram showing connections between internal components of a signal extraction circuit for an ion mobility tube and other peripheral electronic devices according to embodiments of the present disclosure.

In FIG. 4, the DC-blocking module 1 is denoted by a broken-line block. The DC-blocking module 1 may be a separate single electronic device or a circuit formed by multiple electronic devices. The DC-blocking module 1 in the present embodiment may include at least two capacitors connected in series or in parallel with each other. The signal leadin terminal In may be electrically connected to one of the positive or negative polarities of the capacitors, and the signal leadout terminal Out may be electrically connected to the other of the positive or negative polarities of the capacitors.

The capacitors in the present embodiment may be preferably non-polarity capacitors. The capacitors have good behavior of blocking DC and passing AC, and have low cost. When connected in series with each other, each of the capacitors has a lower voltage applied thereon. This facilitates extending the lifecycle of each individual capacitor, and thus improving reliability of the circuit. When several capacitors are connected in parallel, it is possible for the total capacity of the DC-blocking module 1 shown in FIG. 4 to meet the desired requirement, even if capacitors of low capacity are used.

At least two capacitors are connected in series in the present embodiment. Preferably, two capacitors C1 and C2 are connected in series as shown in FIG. 4. Each of the capacitors has a capacitance of 5 to 20 nf. Preferably, the capacitance is 10 nf.

Serial connection of excessive capacitors will added to circuit complexity and cost, while fewer capacitors may cause an excessively large voltage applied on each individual capacitor. It has been proved through practices that serial connection of two capacitors of 5 to 20 nf is sufficient for reliably removing a high voltage up to around 3000V. The capacitance of each capacitor is not limited to the above range, and may be determined based on the magnitude of the voltage on the Faraday plate 21 shown in FIG. 3.

FIG. 2 shows that the ion mobility detector according to embodiments of the present disclosure may include the ion mobility tube 2 shown in FIG. 3.

In the signal extraction circuit for the ion mobility tube shown in the embodiment of FIG. 1, the signal leadin terminal In within the signal extraction circuit is electrically connected to the Faraday plate 21 within the ion mobility tube 2 shown in FIG. 3.

The pulsed voltage processing circuit 3 shown in FIG. 2 is electrically connected to the signal leadout terminal Out. The pulsed voltage processing circuit 3 is configured to perform amplification and/or analog-to-digital conversion on the pulsed voltage output from the signal leadout terminal Out.

Such pulsed voltage is usually of several millivolts. It is easier to obverse the waveform of the pulsed voltage after the pulsed signal amplification circuit within the pulsed voltage processing circuit 3 has amplified the pulsed voltage. Then, it is possible to determine the type of some substance by comparing the waveform of the amplified pulsed voltage with pre-stored waveforms of pulsed voltages corresponding to different types of substances.

The digital-to-analog conversion circuit within the pulsed voltage processing circuit 3 is configured to convert an analog quantity of the waveform of the pulsed voltage to a digital quantity. In this way, it is easier to perform processing, such as display and comparison, by using computer devices having higher information processing capability.

The pre-stored waveforms of pulsed voltages may be detected and recorded prior to substance detection. In the present embodiment, the pulsed voltage processing circuit 3 may be implemented by any existing pulsed voltage processing circuit.

FIG. 3 also shows that an outer shield hood 22 and an inner shield hood 23 are provided within the ion mobility tube 2 in the present embodiment.

The Faraday plate 21 includes first and second sides 211 and 212 located opposite to each other. The first side 211 is configured to receive ions.

The outer shield hood 22 is disposed covering the Faraday plate 21. The convex part of the outer shield hood 22 is opposite to the second side 212 of the Faraday plate 21.

The Faraday plate 21 is electrically connected to an inner core 410 of a first coaxial cable 41 via a connection core wire 24.

The inner shield hood 23 is located within the outer shield hood 22. The convex part of the inner shield hood 23 is disposed opposite to the second side 212 of the Faraday plate 21 and covering the connection core wire 24.

The inner core 410 of the first coaxial cable 41 is electrically connected in parallel with each of the signal leadin terminal In and a first power supply terminal 51 of the ion mobility tube 2 as shown in FIG. 4.

The first outer conductor 411 of the first coaxial cable 41 has its both ends electrically connected to the outer shield hood 22 and a second power supply terminal 52 of the ion mobility tube 2 as shown in FIG. 4, respectively.

The second outer conductor 412 of the first coaxial cable 41 has its both ends electrically connected to the inner shield hood 23 and the first power supply terminal 51, respectively.

As shown in FIG. 3, the connection core wire 24 may be part of the inner core 410 of the first coaxial cable 41, or a separate conductor. Preferably, the connection core wire 24 is obtained by extending the inner core 410 of the first coaxial cable 41, and bending the extension part.

The first power supply terminal 51 is configured to supply high-voltage electric power (preferably, a high voltage of 3000V) to the Faraday plate 21 and the inner shield hood 23, both of which have the same potential. The second power supply terminal 52 is configured to supply high-voltage electric power (preferably, a high voltage of 2970V) to the outer shield hood 22.

The outer shield hood 22 may be used to prevent an electric field between the Faraday plate 21 and the ion source from being interfered by any electric field or interference signal external to the ion mobility tube 2, and thus guarantee detection accuracy.

The electric field between the Faraday plate 21 and the ion source within the ion mobility tube 2 is progressively decreased (for a positive-mode ion mobility tube) or increased (for a negative-mode ion mobility tube) in strength. Accordingly, there is a voltage difference of about 70 to 100V between the outer shield hood 22 and the Faraday plate 21, and electric lines of force will appear therebetween. The inner shield hood 23 can block the electric lines of force between the outer shield hood 22 and the Faraday plate 21. In this way, during substance detection by the ion mobility detector, it is possible to prevent the connection core wire 24 from cutting and blocking the electric lines of force between the outer shield hood 22 and the Faraday plate 21 while the connection core wire 24 is vibrating, and thus to prevent noise caused by such vibration.

It will be understood that in the present embodiment, one or more inner shield hoods 23 may be provided between the outer shield hood 22 of the ion mobility hood 2 and the connection core wire 24, and one or more outer shield hoods may be provided in addition to the outer shield hood 22. The numbers of the outer shield hoods 22 and the inner shield hoods 23 may be determined according to the density of interference signals inside the outer shield hood 22 or outside the ion mobility tube 2. Generally, one inner shield hood 23 may be sufficient for preventing noises caused by the vibration of the connection core wire 24 within the ion mobility tube 2.

As shown in FIG. 3, a suppression net 25 is provided in the ion mobility tube 2, and formed integral with the edge of the outer shield hood 22. The suppression net 25 is located between the ion source and the first side 211 of the Faraday plate 21 in the ion mobility tube 2. The suppression net 25 is formed integral with the outer shield hood 22, and thus is applied with the high voltage of the same value as that applied to the outer shield hood 22. The suppression net 25 may be used in generating a progressively increased or decreased electric field between the ion source and the first side 211 of the Faraday plate 21 in the ion mobility tube 2. This facilitates ions generated by the ion source to target the Faraday plate 21.

In the ion mobility tube 2 of FIG. 3 of the present embodiment, at least one resistor is further connected in series between the first power supply terminal 51 and the inner core 410 of the first coaxial cable 41 as shown in FIG. 4. Preferably, two resistors, R1 and R2, may be connected in series, and each resistor has a resistance of 400 to 600 MΩ. A particularly preferable value is 500 MΩ.

The resistor can block AC current and allow DC current to pass. Accordingly, it is possible to prevent the pulsed voltage output from the first power supply terminal 51 from arriving at the Faraday plate 21 and incurring ripple noise. This will guarantee detection accuracy.

In the case of multiple resistors being connected in series, the voltage applied across each of the resistors is relatively low, thereby guaranteeing reliability and lifespan of the resistors.

As shown in FIG. 4, one of the polarities of at least one filter capacitor is further electrically connected between the first power supply terminal 51 of the ion mobility tube 2 of FIG. 3 and the inner core 410 and the second outer conductor 412 of the first coaxial cable 41. The other polarity of the filter capacitor is grounded.

Preferably, two filter capacitors connected in parallel, C3 and C4, may be provided between the second outer conductor 412 of the first coaxial cable 41 and the ground. The filter capacitors C3 and C4 may have a capacitance of 5 to 20 nf, and preferably 10 nf. The filter capacitors may effectively make the pulsed voltage output from the first power supply terminal 51 grounded, and thus filter out noises output from the first power supply terminal 51. This further guarantees a stable high voltage on the Faraday plate 21 and detection accuracy.

Preferably, the resistors R1, R2 and the filter capacitors C3, C4 are provided together in the signal extraction circuit for the ion mobility tube. Alternatively, either of the resistors R1, R2 or the filter capacitors C3, C4 may be provided together in the signal extraction circuit for the ion mobility tube.

As shown in FIG. 4, the first and second power supply terminals 51 and 52 of the ion mobility tube 2 of FIG. 3 are electrically connected to different high-voltage power supplies V1 and V2 via two core wires 61 and 62 of a two-core cable 6, respectively. The outer shield layer of the two-core cable 6 is grounded.

The first and second power supply terminals 51 and 52 of the ion mobility tube 2 of FIG. 3 are electrically connected to different high-voltage power supplies V1 and V2 via two core wires 61 and 62 of a two-core cable 6, respectively.

The first and second power supply terminals 51 and 52 may be electrically connected to different voltage output terminals in a single high-voltage power supply (e.g., on a single circuit board), or to different high-voltage power supplies V1 and V2 as shown in FIG. 4, via the two core wires 61 and 62 of the two-core cable 6, respectively.

Electric power from the first and second power supply terminals 51 and 52 may be transmitted through the two core wires 61 and 62 of the two-core cable 6, respectively. Accordingly, interference between the two wires of different voltages can be prevented. It will be understood that the first and second power supply terminals 51 and 52 may be electrically connected to the different high-voltage power supplies V1 and V2 via two different common cables.

In the embodiment, of FIG. 4, the signal leadout terminal Out is electrically connected to the second coaxial cable 42, and the pulsed voltage output from the signal leadout terminal Out is output via the inner core of the second coaxial cable 42. The outer conductor of the second coaxial cable 42 is grounded.

The second coaxial cable 42 can lead the pulsed voltage output from the signal leadout terminal Out into the pulsed voltage processing circuit 3 of FIG. 2. Further, the outer conductor of the second coaxial cable 42 can shield the pulsed voltage from interference of other peripheral signals.

In the embodiment of FIG. 4, the first and second coaxial cables 41 and 42 are each a tri-coaxial cable. The first outer conductor 411 is the outer shield layer of the tri-coaxial cable, and the second conductor 412 is the inner shield layer of the tri-coaxial cable.

The tri-coaxial cable is preferably formed of materials, such polytetrafluoroethylene. The ordinary tri-coaxial cable costs much lower than any existing high-voltage cable. The voltage difference between the first and second outer conductors 411 and 412 of the first coaxial cable 41 in the present embodiment is preferably in the range of 70 to 100V. The ordinary tri-coaxial cable can withstand a voltage of 200V, and thus can be used in the present embodiment. Meanwhile, the inner core, outer shield layer and inner signal layer of a single tri-coaxial cable may be electrically connected to the Faraday plate 21, the outer shield hood 22 and the inner shield hood 23, respectively, and thus functions as three individual high-voltage cables. The connection of a single tri-coaxial cable with the Faraday plate 21, the outer shield hood 22 and the inner shield hood 23 is simpler than the connection of three ordinary high-voltage cables with the Faraday plate 21, the outer shield hood 22 and the inner shield hood 23, respectively. This contributes to less difficult in implementing such connection. Accordingly, use of the tri-coaxial cable can effectively reduce cost of the signal extraction circuit for the ion mobility tube. Besides the tri-coaxial cable, the first and second coaxial cables 41 and 42 of the present embodiment may be implemented by some other coaxial cable, such as quad-coaxial cable. In this case, the additional outer conductor of the quad-coaxial cable needs to be grounded.

The signal extraction circuit for the ion mobility tube in the present embodiment may be provided on a circuit board and housed together with the circuit board within a package of potting glue. The potting glue package may be further covered by a grounded, metal shield hood 11 shown in FIG. 4.

Providing the signal extraction circuit for the ion mobility tube on the circuit board will facilitate mass production in integrated circuit manufacture process, and shipment and replacement of the circuit board.

The potting glue is good insulator. The potting process involves placing a circuit board carrying circuits in the fluid of potting glue. The circuit board and the circuits on the board can be protected by the potting glue after the potting glue is solidified. Use of the potting glue can provide good insulation between the respective unconnected circuits or lines within the signal extraction circuit, and firmly hold these circuits or lines to their locations. This improves the weathering resistance and lifespan of the circuits. The metal shield hood 11 of FIG. 4 can provide good electromagnetic shield for the solidified potting glue, and thus prevent influences from external signals on the signal extraction circuit, thereby ensuring that the signal extraction circuit is reliable and able to extracts a clean pulsed voltage. The metal shield hood 11 can also protect the potting glue and the signal extraction circuit within the potting glue. This contributes to lifespan and weathering resistance of the signal extraction circuit.

The respective grounded devices in the above embodiment may be connected to the same or different grounds according to their electrical requirements.

The ion mobility detector in the above embodiment is preferably implemented as a dual-mode ion mobility detector having both positive and negative ion mobility zones.

Such dual-mode ion mobility detector having both positive and negative ion mobility zones can detect both positive and negative ions, and is more powerful and applicable to implement the above solutions of the present disclosure. It will be understood that the above solutions of the present disclosure can be also implemented with a single-mode ion mobility detector having one of positive and negative ion mobility zones.

Figure 5:
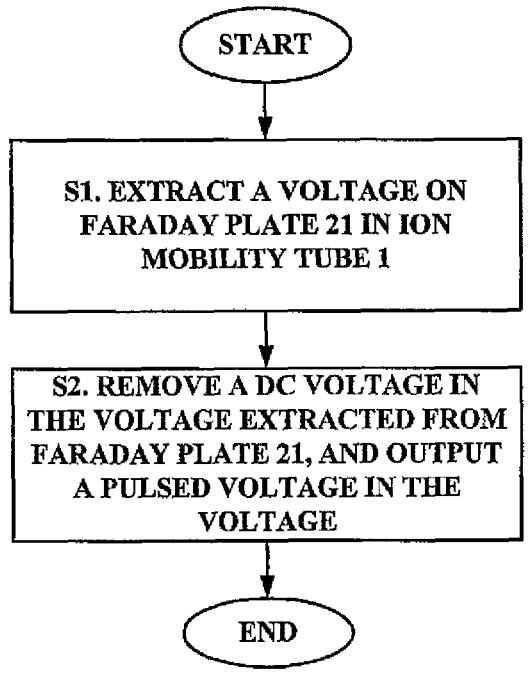
FIG. 5 is a schematic diagram showing an internal flow of a signal extraction method for an ion mobility tube according to embodiments of the present disclosure.

A signal extraction method for the ion mobility tube according to embodiments of the present disclosure will be illustrated with reference to FIGS. 2 and 5.

At step S1, a voltage is first extracted out from the Faraday plate 21 in the ion mobility tube 2.

Then, at step S2, the DC voltage contained in the voltage extracted out from the Faraday plate 21 is removed, and then the pulsed voltage contained in the voltage is output.

Like the signal extraction circuit for the ion mobility tube provided in the above embodiment, the signal extraction method can also solve the problem with the conventional technologies that it is difficult to design and manufacture the leadout circuit for the pulsed voltage on the Faraday plates. It will be understood that the signal extraction method may also be implemented with some other circuit except the DC-blocking module 1 shown in FIG. 2.

The foregoing description of the embodiments is intended for illustrating the present invention, and thus should not be construed as limiting the present invention. Those ordinarily skilled in the art will appreciate that although the present invention is described with preferred embodiments, modifications or substitutions can be made on the embodiments or part of them within the scope of the present invention, and all such modifications and substitutions shall fall into the scope of the present invention.

What is claimed is:

1. An ion mobility detector, comprising:
   an ion mobility tube operable to characterize ions from an ion source by detecting mobility of the ions in an electric field;
   a signal extraction circuit, comprising a DC blocking module provided with a signal leadin terminal and a signal leadout terminal, wherein the signal leadin terminal in the signal extraction circuit is electrically connected to a Faraday plate in the ion mobility tube, and the DC blocking module is configured to block a high voltage bias signal contained in a voltage from the Faraday plate while passing a time-varying low voltage waveform contained in the voltage extracted from the Faraday plate representing ions received at the Faraday plate as a result of the high voltage bias signal applied to the Faraday plate;
   a pulsed voltage processing circuit electrically connected to the signal leadout terminal and operating at a low voltage, the pulsed voltage processing circuit being configured to perform amplification and/or analog-to-digital conversion on the pulsed voltage output from the signal leadout terminal, wherein an outer shield hood and an inner shield hood are further provided in the ion mobility tube;
   the Faraday plate comprises first and second sides located opposite to each other, and the first side is configured to receive ions;
   the outer shield hood is disposed covering the Faraday plate, and a convex part of the outer shield hood is located opposite to the second side of the Faraday plate;
   the Faraday plate is electrically connected to an inner core of a first coaxial cable via a connection core wire;
   the inner shield hood is located inside the outer shield hood, and a convex part of the inner shield hood is located opposite to the second side of the Faraday plate and disposed covering the connection core wire;
   the inner core of the first coaxial cable is electrically connected in parallel to the signal leadin terminal and a first power supply terminal of the ion mobility tube, respectively;
   both ends of a first outer conductor of the first coaxial cable are electrically connected to the outer shield hood and a second power supply terminal of the ion mobility tube, respectively;

both ends of a second outer conductor of the first coaxial cable are electrically connected to the inner shield hood and the first power supply terminal, respectively.

2. The signal extraction circuit for an ion mobility detector of claim 1, wherein the DC blocking module comprises at least two capacitors connected in series with each other, thereby reducing the required voltage rating needed for each series capacitor relative to a single equivalent capacitor, the signal leadin terminal is connected to one of a positive polarity or a negative polarity of the capacitors, and the signal leadout terminal is connected to the other of the positive or negative polarity of the capacitors.

3. The ion mobility detector of claim 2, wherein each of the capacitors has a capacitance of 5 nf to 20 nf.

4. The ion mobility detector of claim 1, wherein at least one resistor is connected in series between the first power supply terminal of the ion mobility tube and the inner core of the first coaxial cable; and/or
one of the polarities of at least one filter capacitor is further electrically connected between the first power supply terminal of the ion mobility tube and the inner core and the second outer conductor of the first coaxial cable, and the other polarity of the filter capacitor is grounded; and/or
the first and second power supply terminals of the ion mobility tube are electrically connected to different high-voltage power supplies via two core wires of a two-core cable, respectively, and an outer shield layer of the two-core cable is grounded.

5. The ion mobility detector of claim 4, wherein the resistor has a resistance of 400 MΩ to 600 MΩ; and/or the signal leadout terminal is electrically connected to a second coaxial cable, and the pulsed voltage output from the signal leadout terminal is output from an inner core of the second coaxial cable, and an outer conductor of the second coaxial cable is grounded.

6. The ion mobility detector of claim 5, wherein the first and second coaxial cables are each a tri-coaxial cable, the first outer conductor is an outer shield layer of the tri-coaxial cable, and the second outer conductor is an inner signal layer of the tri-coaxial cable.

7. The ion mobility detector of claim 1, wherein the signal extraction circuit for the ion mobility tube is provided on a circuit board, and packaged together with the circuit board in a potting glue; the potting glue is further covered with a grounded metal shield hood; and/or the ion mobility detector is a dual-mode ion mobility detector having positive and negative ion mobility zones.

* * * * *